US008311616B2

(12) United States Patent
Feldman et al.

(10) Patent No.: US 8,311,616 B2
(45) Date of Patent: Nov. 13, 2012

(54) METHOD AND SYSTEM FOR DETERMINATION OF PHYSIOLOGICAL CONDITIONS AND EMOTIONAL STATES OF A LIVING ORGANISM

(75) Inventors: Yuri Feldman, Jerusalem (IL); Paul Ben-Ishai, Modiin (IL); Alexander Puzenko, Jerusalem (IL); Andreas Caduff, Zurich (CH); Aharon Agranat, Mevasseret Zion (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 977 days.

(21) Appl. No.: 11/921,042

(22) PCT Filed: May 17, 2006

(86) PCT No.: PCT/IL2006/000579
§ 371 (c)(1),
(2), (4) Date: Sep. 5, 2008

(87) PCT Pub. No.: WO2006/126186
PCT Pub. Date: Nov. 30, 2006

(65) Prior Publication Data
US 2009/0281414 A1    Nov. 12, 2009

(30) Foreign Application Priority Data
May 26, 2005 (IL) .......................... 168839

(51) Int. Cl.
*A61B 5/05* (2006.01)
(52) U.S. Cl. .................................. 600/430
(58) Field of Classification Search ......... 600/430; 607/101; 250/250; 342/22; 324/637
See application file for complete search history.

(56) References Cited

U.S. PATENT DOCUMENTS

| 4,958,638 A | 9/1990 | Sharpe et al. |
| 5,131,409 A | 7/1992 | Lobarev et al. |
| 5,458,142 A | 10/1995 | Farmer et al. |

(Continued)

FOREIGN PATENT DOCUMENTS

EP     0 447 568     9/1991

(Continued)

OTHER PUBLICATIONS

Gat et al., "Olfactory receptor protein: expression, characterization and partial purification." *Eur. J. Biochem.*, v.225, pp. 1157-1168 (1994).

(Continued)

*Primary Examiner* — Jacqueline Cheng
(74) *Attorney, Agent, or Firm* — Vorys, Sater, Seymour and Pease LLP; Susanne M. Hopkins

(57) ABSTRACT

A method and system for non-invasive determination of at least one condition of a living organism selected from physiological conditions and emotional states of the living organism are described. The method comprises sensing electromagnetic waves emanated from a skin portion in an extremely high frequency (EHF) band, and obtaining from the sensed electromagnetic waves at least one unique biometric signature of the living organism indicative of the organism condition. The system includes an antenna array unit configured for sensing the electromagnetic waves emanated from the skin portion; and a receiving unit configured and operable for obtaining the unique biometric signature. The sensed electromagnetic waves are indicative of bioelectric activity of neurally connected and electromagnetically interacting structures distributed in a skin portion of the living organism.

32 Claims, 9 Drawing Sheets

U.S. PATENT DOCUMENTS

| | | | | |
|---|---|---|---|---|
| 5,507,291 | A | 4/1996 | Stirbl et al. | |
| 5,507,791 | A | 4/1996 | Sit'ko | |
| 5,788,648 | A | 8/1998 | Nadel | |
| 6,217,604 | B1 | 4/2001 | Azure et al. | |
| 6,957,099 | B1 * | 10/2005 | Arnone et al. | 600/473 |
| 7,180,441 | B2 * | 2/2007 | Rowe et al. | 342/22 |
| 7,725,151 | B2 * | 5/2010 | van der Weide | 600/407 |

FOREIGN PATENT DOCUMENTS

| | | |
|---|---|---|
| RU | 2 066 557 | 9/1996 |
| WO | 00/50859 | 8/2000 |
| WO | 01/93746 | 12/2001 |
| WO | 2004/038854 | 5/2004 |
| WO | 2005/092191 | 10/2005 |

OTHER PUBLICATIONS

Nekrasova et al., "Overexpression, solubilization and purification of rat and human olfactory receptors." *Eur. J. Biochem.*, v.238, pp. 28-37 (1996).

Gat et al., "De Novo hair follicle morphogenesis and hair tumors in mice expressing a truncated betacatenin in skin." *Cell*, v.95, pp. 605-614 (1998).

Chan et al., "A common human skin tumour is caused by activating mutations in beta-catenin." *Nature Genetics*, v.21, pp. 410-413 (1999).

Merrill et al., "Tcf3 and Lef1 regulate lineage differentiation of multipotent stem cells in skin." *Genes and Development*, v.15, pp. 1688-1705 (2001).

Levanon et al., "Spatial and temporal expression pattern of Runx3 (Am12) and Runx1 (Am11) indicates non-redundant functions during mouse embryogenesis." *Mechanisms of Development*, v.109, pp. 413-417 (2001).

Huemmerich et al., "Novel assembly properties of recombinant spider dragline silk proteins." *Current Biology*, v.14, pp. 2070-2074 (2004).

Ohhashi et al., "Human perspiration measurement." *Physiol. Meas.*, v.19, pp. 449-461 (1998).

Nicander et al., "Electrical impedance measurements at different skin sites related to seasonal variations." *Skin Research & Tech.*, v.6, pp. 81-86 (2000).

Caduff et al., "First human experiments with a novel non-invasive, non-optical continuous glucose monitoring system." *Biosensors and Bioelectronics*, v.19, pp. 209-217 (2003).

Alberts et al., *Molecular Biology of the Cell*. Third Edition, Garland Publishing Inc. (1994). (Cover page and contents only.)

Granger et al., "Na+/H+ exchangers in the human eccrine sweat duct." *Am. J. Physiol. Cell Physiol.*, v.285, pp. C1047-C1058 (2003).

Krasnoholovets et al., "Proton transfer and coherent phenomena in molecular structures with hydrogen bonds." *Adv. Chem. Phys.*, v.125, pp. 351-548 (2004).

Naito et al., "Microwave dielectric analysis of human stratum corneum in vivo." *Biochimica et Biophysica Acta*, v.1381, pp. 293-304 (1998).

Malmivuo et al., *Bioelectromagnetism*, University Oxford Press. Oxford, New York (1995). (Cover page and contents only.)

Reshetnyak et al., "Mechanisms of interaction of electromagnetic radiation with a biosystem." *Laser Physics*, v.6, pp. 621-653 (1996).

Hadjiloucas et al., "Preliminary results on the non-thermal effects of 200-350, GHz radiation on the growth rate of *S. cerevisiae* cells in microcolonies." *Phys. in Med. and Bio.*, v.47, pp. 3831-3839 (2002).

H. Frölich, "The biological effects of microwaves and related questions." *Advances in Electronics and Electron Physics*, v.53, pp. 85-152 (1980).

Pakhomov et al., "Current state implications of research on biological effects of millimeter waves." *Bioelectromagnetics*, v.19(7), pp. 393-413 (1998).

Pakhomov et al., "Low-intensity millimeter waves as a novel therapeutic modality." IEEE Transactions on plasma science, v.28, pp. 34-40 (2000).

Woodward et al., "Terehertz pulse imaging in reflection geometry of human skin cancer and skin tissue." *Physics in Medicine and Biology*, v.47(21), pp. 3853-3863 (2002).

Feldman, Y., et al., "Human Skin as Arrays of Helical Antennas in the Millimeter and Submillimeter Wave Range", PRL, vol. 100, pp. 128102-1-128102-4, (2008).

\* cited by examiner

METHOD AND SYSTEM FOR DETERMINATION OF PHYSIOLOGICAL CONDITIONS AND EMOTIONAL STATES OF A LIVING ORGANISM

FIELD OF THE INVENTION

This invention is generally in the field of non-invasive identification and monitoring techniques and relates to a system and method for communicating with a living organism using electromagnetic waves in the millimeter and sub-millimeter wavelength region.

BACKGROUND OF THE INVENTION

Living organisms are full of electrical signals which produce electromagnetic waves in a broad frequency (wavelength) range. These electromagnetic waves arise from electrical activity within the organism, such as metabolic respiration, nerve impulses, muscle contractions, piezoelectric effects of bone and skin, brain activity, and therefore reflect the physiological condition and emotional state of the organism. According to oriental philosophies, illness is believed to be the result of a lack of or imbalance in the "energy field" in and around the body and can be observed by examining the field. Body electric signals and electromagnetic fields can be measured and analyzed non-invasively through the use of various techniques.

For example, the measurements of electromagnetic radiation produced by the brain can lead to an understanding of the mechanisms of functioning, perception and sensory response (see, for example, U.S. Pat. No. 5,788,648 to Nadel).

Thermal analysis has been used as a medical diagnostic technique for years. It is well understood that higher temperatures exist near injuries than in surrounding tissue. Thermal imaging can be conducted by contacting thermal sensors or by infrared sensitive cameras.

A method and system for monitoring the physiological and emotional state, and the changes in the physiological and emotional state, of a living organism by means of the electromagnetic emissions of the organism are disclosed in U.S. Pat. No. 5,458,142 to Farmer et al. The system described by Farmer et al for diagnostic and therapeutic purposes utilizes a coil of conductive material for sensing magnetic fields originating from an organism in the low frequency range of 0.1 Hz to 30 Hz.

A number of techniques have been developed for the application of electromagnetic radiation for treatment or health benefit purposes.

For example, European Patent No. 0 447 568 and U.S. Pat. No. 5,131,409 to Lobarev et al describe an apparatus for therapy by microwave resonance. The apparatus employs the millimeter wavelength band that corresponds to the frequency range of 25 GHz to 180 GHz for applying to biologically active patient's body points in the patient.

U.S. Pat. No. 5,507,791 to Sit'ko describes a method of treating the patient by applying electromagnetic radiation in the microwave frequency range to a set of biologically active points. The frequency and power of the radiation applied are varied in the ranges of 52 GHz to 62 GHz and $10^{-20}$ W/Hz·cm$^2$ to $10^{-10}$ W/Hz·cm$^2$, respectively, so as to determine a frequency and power level which promote a steady response reaction of the patient in the desired area of treatment.

U.S. Pat. No. 6,217,604 to Azure et al describes a method for the therapeutic treatment of diseased cells in a patient. An electromagnetic field is generated and the patient exposed to the electromagnetic field. The electromagnetic field may be a pulsed electromagnetic field and may be used for the treatment of a patient having AIDS. The method may also comprise exposing the patient to an electromagnetic field having frequencies in a visible spectrum in combination with an electromagnetic field having frequencies not in the visible spectrum (up to 2 GHz), such as may be useful to treat a variety of conditions.

SUMMARY OF THE INVENTION

The present invention is based on the appreciation that some of the neurally connected structures distributed in the skin of a living organism may provide electromagnetically active functionality. This enables communication with the living organism using electromagnetic radiation. Hereinafter, the term "communication" stands for either one or both of the following effects: radiation detection (reception of electromagnetic waves emanated from the skin) and radiation stimulation/excitation of the skin (transmission of electromagnetic radiation to the skin). Thus, the present invention utilizes the fact that some of the neurally connected structures distributed in the skin may provide electromagnetically active functionalities. For example, being filled with electrolytes (such as Na$^+$ and Cl$^-$ in water) spiral sweat ducts can be considered as the organic equivalent of inductance coils in electric circuits. Hence, their coupling with the known capacitance and resistance of the human skin raises the possibility of considering the human skin as a spatial distribution of circuits composed of resistors, capacitors and inductors (RCL resonant circuits).

Each of the resonant circuits can produce electromagnetic oscillation characterized by the corresponding resonant frequency. Hence, the skin can be considered as a phased antenna array, where each individual sweat gland/duct could act as an antenna element for reception and transmission of electromagnetic waves. In particular, fast proton currents, mediated by hydrogen bonded networks in the cells of the sweat duct wall, could provide the carrier current of the system, while modulation of amplitude and phase can be provided by the electrolyte current of sweating. The resulting radiation pattern can be influenced by the start time for sweating of each gland, the spatial distribution of sweat glands on the skin surface, the variations of resonant frequencies of the individual glands, the different rates of perspiration through the glands and other factors.

There is a need in the art for a technique for detection of electromagnetic waves associated with bioelectric activity of neurally connected and electromagnetically interacting structures distributed in a skin of the living organism.

Examples of the living organisms include, but are not limited to, human beings and some sorts of mammals.

An example of the neurally connected and electromagnetically interacting structures distributed in a skin includes, but is not limited to, sweat glands.

It would be advantageous to employ an individual pattern of sweat gland distribution in each person, which can allow to utilize unique bioelectric signatures associated with the bioelectric activity of sweat glands (e.g., eccrine sweat glands) for human identification, diagnostics and treatment.

The present invention satisfies the aforementioned need by providing a method for non-invasive determination of at least one condition of a living organism on the basis of detection of electromagnetic waves produced as a result of bioelectric activity of sweat glands distributed in a skin portion of a living organism. The organism condition is selected from physiological condition and emotional state of the living organism. Examples of physiological condition include, but are not limited to, the conditions caused by exercise, environmental conditions, (e.g., temperature and humidity), illness, puberty, menopause, menstruation, metabolism, etc. Examples of emotional state include, but are not limited to, stress, anxiety fear, anger, nervousness, embarrassment, panic, general neurological disorders, etc.

According to one aspect of the invention, the concept of detection of electromagnetic waves produced as a result of bioelectric activity of sweat glands is utilized for the radiation detection in a so-called passive mode.

The method for passive detection includes sensing the electromagnetic waves emanated from the skin portion in the frequency range of about 30 GHz to 1 THz. This sensing frequency region includes the frequency band of 30 GHz to 300 GHz (which is usually referred in the art as the Extremely High Frequency Range (EHF)), and also the higher electromagnetic radiation (which considered to be a part of Low (or Far) Infrared Radiation). The sensing frequency range used by the present invention has a wavelength of about 0.3 millimeters to ten millimeters, giving it the name sub-millimeters to millimeters band. It should be noted that although this sensing range extends the conventional EHF band, for the conciseness purpose, the entire sensing range between 30 GHz to 1 THz hereinafter will be referred to as the Extremely High Frequency (EHF) range, without derogation of the invention.

The method of the present invention also includes obtaining from the sensed electromagnetic waves one or more biometric signatures and, when required, one or more signature characterizing parameters associated with the bioelectric activity of the sweat glands. The biometric signatures and the signature characterizing parameters are indicative of the conditions of the living organism that may effect sweating, e.g., physiological condition and/or emotional state of the living organism.

According to an embodiment of the invention, the step of obtaining of the biometric signatures includes producing an extremely high frequency (EHF) electromagnetic signal based on the sensed EHF electromagnetic waves. The EHF electromagnetic signal is an EHF carrier signal modulated by a low frequency information signal related to the bioelectric activity of the sweat glands. The obtaining of the biometric signatures also includes heterodyning the EHF signal from its extremely high carrier frequency band to a lower frequency band to produce an intermediate frequency electromagnetic signal. Then, the intermediate frequency electromagnetic signal can be demodulated to provide the low frequency information signal representing one or combination of several modulating functions. The modulating functions can be selected from an amplitude modulating function, frequency modulating function, and phase modulating function.

The obtaining of the biometric signatures further includes converting the low frequency information signal from analog form to digital form to produce a digitalized information signal. Thereafter, the digitalized information signal is analyzed for determining the biometric signatures.

According to one embodiment of the invention, the analyzing of the digitalized information signal is carried out in frequency domain. In this case, the biometric signature can be in the form of a frequency spectrum of the digitalized information signal.

According to another embodiment of the invention, the analyzing of the digitalized information signal is carried out in time domain. In this case, the analyzing of the digitalized information signal further includes processing the digitalized information signal through the Fourier transform, thereby obtaining the biometric signatures in the form of an autocorrelation function of the digitalized information signal.

When required, the analyzing of the digitalized information signal further includes determining one or more biometric characteristic parameters derived from the behavior of the biometric signatures. For example, when the analyzing of the digitalized information signal is carried out in frequency domain, the parameters describing behavior of the frequency spectra can be selected as characteristic parameters. Examples of such parameters include, but are not limited to, frequency values at which peaks on the frequency spectra occur, amplitudes of these peaks and Q-factor of these peaks.

In turn, when the analyzing of the digitalized information signal is carried out in time domain, the parameters describing behavior of a time autocorrelation function of the digitalized information signal and/or parameters describing cross correlation of the signal with a previously determined information signal can be selected as characteristic parameters. Examples of biometric characteristic parameters include, but are not limited to, the amplitude of the correlation function and effective correlation times of the peaks.

According to an embodiment of the invention, the method for non-invasive determination of the condition of a living organism can be utilized for identification of the living organism. In such a case, the method further includes the step of providing predetermined reference data sensitive to organism individuality and indicative of the sweat related conditions for a group of living organisms. The predetermined reference data can include biometric signatures and/or characterizing parameters derived from the signatures for each organism from the group of the organisms.

Then, the method utilized for identification includes comparing at least one biometric signature or at least one biometric characterizing parameter derived from the biometric signatures of the living organism wider identification with the predetermined reference data. Thereafter, the method includes estimating from this comparison to which of the organisms from the group of organisms the biometric signature or the characterizing parameter corresponds.

According to another embodiment of the invention, the method for non-invasive determination of the condition of a living organism can be utilized for diagnostics of the living organism. In this case, the method further includes providing predetermined reference data sensitive to organism individuality and indicative of different conditional states (e.g., a healthy state and/or diseases) from a predetermined list of diseases. In this case, the predetermined reference data include biometric signatures and/or characterizing parameters derived therefrom corresponding to each disease from the predetermined list of conditional states.

Then, at least one biometric signature or at least one biometric characterizing parameter derived from the signature of the living organism under diagnostics is compared with the predetermined reference data. Thereafter, the method includes estimating from this comparison to which of the conditional states from the predetermined list of conditional states the biometric signature or the characterizing parameter corresponds.

According to yet another embodiment of the invention, the method of the invention for determination of biometric signatures and/or characterizing parameter can be utilized for determining which condition the living organism has. In such a case, the method further comprises providing predetermined reference data of at least one biometric signature or at least one characterizing parameter derived therefrom from a plurality of living organisms diagnosed for a first condition. Then this step is repeated to provide a series of reference data, each corresponding to a different condition. Thereafter, the method includes comparing the biometric signatures and/or the characterizing parameters of the living organism under examination with each one of the predetermined reference data in said series. Then, the method includes determining which reference data has statistically significant similarity with the biometric signature or the characterizing parameter of the living organism under examination, thereby the condition for which the reference data has statistically significant similarity is the condition of the living organism.

According to another aspect of the invention, the concept of detection of electromagnetic waves produced as a result of bioelectric activity of sweat glands can also be utilized for the detection in an active mode.

The method for active detection before the sensing of the electromagnetic waves emanated from the skin portion further comprises preparing a predetermined modulated high frequency signal. The predetermined modulated high frequency signal is an EHF carrier signal modulated by a predetermined low frequency information signal. The method for active detection also includes generating a predetermined modulated electromagnetic wave based on the modulated high frequency signal, and applying the predetermined modulated electromagnetic wave to the skin portion. Thereafter, all the method steps of the passive detection described above can be applied for identification and diagnostics applications.

It is likewise possible to employ a predetermined modulated electromagnetic wave in the extremely high frequency range for therapeutic treatment. In particular, the predetermined modulated electromagnetic wave being an EHF carrier signal modulated by a predetermined information signal can be applied to the skin of a living organism. The predetermined information signal can include information for modifying its sweat related condition, such as physiological condition and emotional state.

Moreover, the applying of electromagnetic waves can be utilized for correcting the bioelectric activity of the neurally connected and electromagnetically interacting structures (e.g., sweat glands) distributed in the skin, and thereby providing therapeutic treatment to the organism. In such a case, the amplitude, frequency and/or phase modulation functions detected from a healthy organism can be used for modulating the EHF carrier signal. When such an EHF signal modulated by a modulation function bearing the information of a healthy organism is applied to an ill organism, this information can be conveyed to the spinal cord and brain to regulate the functioning of the organism.

The present invention also satisfies the aforementioned need by providing a system for non-invasive determination of at least one condition of a living organism.

According to one embodiment of the invention, the system includes an antenna array Unit and a receiving unit coupled to the antenna array. The antenna array unit is configured for sensing the electromagnetic waves emanated from the skin portion in the EHF range and producing an EHF electromagnetic signal based on the sensed electromagnetic waves. The high frequency electromagnetic signal is an EHF carrier signal modulated by a low frequency information signal related to the bioelectric activity of the neurally connected and electromagnetically interacting structures. The receiving unit is configured for obtaining from the EHF electromagnetic signal based on sensed electromagnetic waves one or more biometric signatures associated with the bioelectric activity of the structures (e.g., sweat glands).

According to an embodiment of the invention, the receiving unit includes a heterodyne unit coupled to the antenna array. The heterodyne unit is operable to transfer the EHF electromagnetic signal from its extremely high carrier frequency band to a lower frequency band, thereby to produce an intermediate frequency electrical signal.

The receiving unit also includes a demodulator downstream of the heterodyne unit. The demodulator is configured for demodulating the intermediate frequency electrical signal, thereby to provide the information signal representing at least one modulating function selected from an amplitude modulating function, frequency modulating function, and phase modulating function.

The receiving unit further includes an analog-to-digital (A/D) converter coupled to the demodulator and configured for converting the low frequency information signal from analog form to digital form to produce a digitalized information signal.

The receiving unit yet includes a control system coupled to the A/D converter and configured for analyzing the digitalized information signal for determining the biometric signatures and/or characterizing parameters derived from the signatures.

When required, the receiving unit can include an intermediate frequency amplifier coupled to the heterodyne unit and configured for amplifying said intermediate frequency electrical signal to produce an amplified intermediate frequency electrical signal.

When required, the receiving unit can also include an EHF frequency amplifier arranged downstream of the antenna array and upstream of the heterodyne unit. The EHF frequency amplifier is configured for amplifying the EHF electromagnetic signal before feeding thereof to the heterodyne unit.

According to an embodiment of the invention, the heterodyne unit includes a heterodyne generator, a mixer coupled to the heterodyne generator, a non-liner element coupled to the mixer and a low pass filter downstream of the non-liner element. An example of the non-liner element includes, but is not limited to, a diode.

According to the invention, the demodulator includes at least one modulation module selected from an amplitude modulation module, a frequency modulation module and a phase modulation module.

According to an embodiment of the invention, the control system includes a memory unit configured for storing, inter alia, predetermined reference data sensitive to organism individuality and indicative of one or more sweat related condition for a group of organisms. The predetermined reference data can be in the form of a database containing one or more records establishing correlation between the biometric signatures and the corresponding sweat related conditions.

According to this embodiment, the system is configured to provide identification of the living organism. In such a case, the control system is operable to compare the biometric signatures or characterizing parameters derived from the signatures of the living organism under identification with the predetermined reference data; and to estimate from this comparison to which of the organisms from the group of organisms these biometric signature or the characterizing parameters correspond.

According to another embodiment of the invention, the system is configured to provide diagnostics of the living organism. In this case, the control system includes a memory unit configured for storing, inter alia, predetermined reference data sensitive to organism individuality and indicative of different conditional states (e.g., healthy state and/or diseases) from a predetermined list of conditional states. The predetermined reference data are in the form of a database containing one or more records establishing correlation between the biometric signatures and the corresponding diseases from the predetermined list of diseases. According to this embodiment, the system is configured for comparing the biometric signatures or characterizing parameters derived therefrom of the living organism under diagnostics with the predetermined reference data, and estimating from this comparison to which of the conditional states from the predetermined list of conditional states the biometric signatures or characterizing parameters correspond.

According to an embodiment of the invention, the system can operate in an active mode. In this case, the system further comprises a transmitting unit coupled to the control system, and a transmitting antenna coupled to the transmitting unit. The transmitting unit includes an EHF signal generator coupled to the control system and responsive to a switch control signal provided thereby. The EHF signal generator is operable to generate an EHF carrier signal sampled over time which includes one or more pulses of predetermined high frequencies.

The transmitting unit also includes a modulator coupled to the EHF signal generator and the control system. The modulator of the transmitting unit is responsive to a modulation control signal provided by the control system and configured for applying a predetermined low frequency information signal (which is represented by at least one predetermined modulation function) to the EHF generator to modulate the EHF carrier signal.

When required, the transmitting unit can include an EHF amplifier coupled to the EHF generator and configured for amplifying the modulated EHF carrier signal. The transmitting antenna can be coupled to the EHF amplifier of the transmitting unit and configured for generating and radiating electromagnetic waves based on the EHF frequency modulated signals towards the living organism.

In the system according to this embodiment, the predetermined low frequency information signal can include information for modifying one or more sweat related conditions. Likewise, the predetermined low frequency information signal can include information for providing a therapeutic treatment to the living organism.

In summary, according to one broad aspect of the present invention, there is provided a method for non-invasive determination of at least one condition of a living organism selected from physiological conditions and emotional states of the living organism, the method comprising:

sensing electromagnetic waves emanated from a skin portion in an extremely high frequency (EHF) band, the sensed electromagnetic waves being indicative of bioelectric activity of neurally connected and electromagnetically interacting structures distributed in a skin portion of the living organism; and obtaining from the sensed electromagnetic waves at least one unique biometric signature of the living organism indicative of said at least one organism condition.

According to another broad aspect of the present invention, there is provided a system for non-invasive determination of at least one condition of a living organism selected from physiological conditions and emotional states of the living organism, the system comprising:

an antenna array unit configured for electromagnetic waves emanated from the skin portion in an extremely light frequency (EHF) band, and producing a EHF electromagnetic signal based on the sensed electromagnetic waves, said EHF electromagnetic signal being a EHF carrier signal modulated by a low frequency information signal associated with bioelectric activity of neurally connected and electromagnetically interacting structures distributed in a skin portion of the living organism; and a receiving unit coupled to the antenna array and configured and operable for obtaining from said EHF electromagnetic signal based on sensed electromagnetic waves at least one unique biometric signature of said living organism Indicative of said at least one organism condition.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

In order to understand the invention and to see how it may be carried out in practice, preferred embodiments will now be described, by way of non-limiting examples only, with reference to the accompanying drawings, in which.

DETAILED DESCRIPTION OF THE INVENTION

Figure 1:
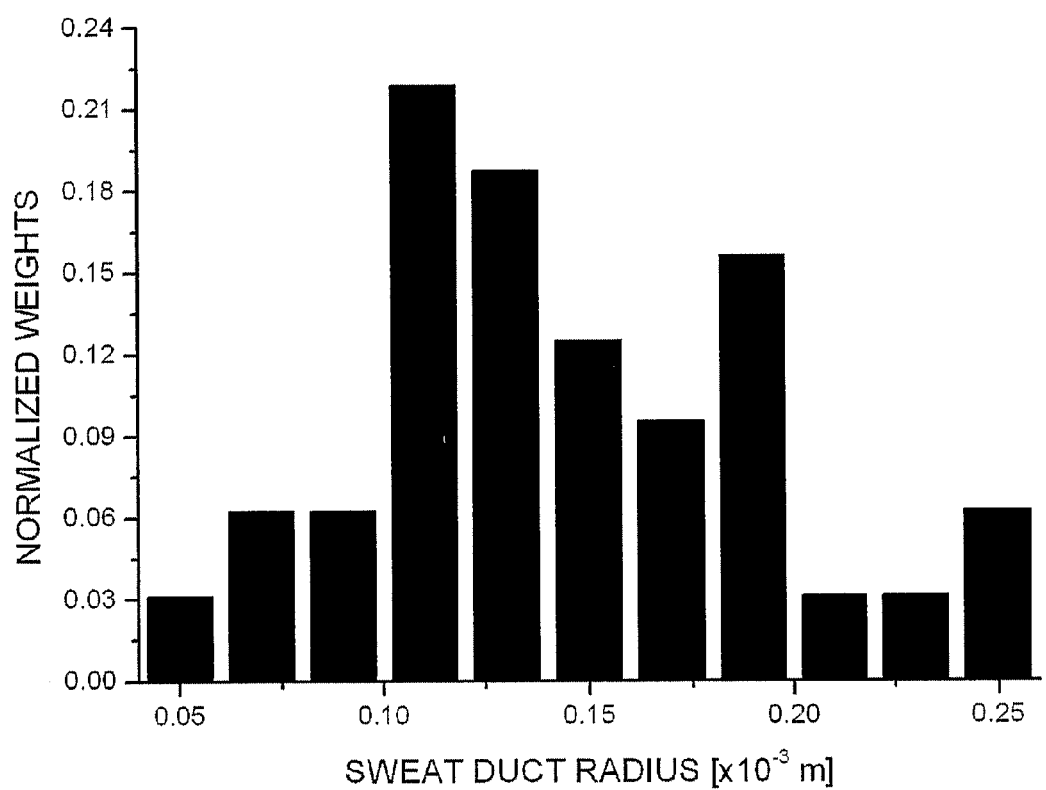
FIG. 1 illustrates an example of distribution of sweat pores radius on a human thumb.

The principles and operation of the system and method of the present invention for detection of electromagnetic waves produced as a result of bioelectric activity of eccrine sweat glands of a living organism may be better understood with reference to the drawings and the accompanying description, it being understood that these drawings and examples in the description are given for illustrative purposes only and are not meant to be limiting. The same reference Roman numerals and alphabetic characters will be utilized for identifying those components which are common in the system for detection of radiation originated from eccrine sweat glands and its components shown in the drawings throughout the present description of the invention. It should be noted that the blocks in the drawings illustrating various embodiments of the present invention are intended as functional entities only, such that the functional relationships between the entities are shown, rather than any physical connections and/or physical relationships.

Some portions of the detailed descriptions, which follow hereinbelow, are presented in terms of algorithms and symbolic representations of operations on data represented as physical quantities within registers and memories of a computer system. An algorithm is here conceived to be a sequence of steps requiring physical manipulations of physical quantities and leading to a desired result. Usually, although not necessarily, these quantities take the from of electrical or magnetic signals capable of being stored, transferred, combined, compared, and otherwise manipulated. In the present description, these signals can be referred to as values, elements, symbols, terms, numbers, or the like.

Unless specifically stated otherwise, throughout the description, utilizing terms such as "processing" or "computing" or "calculating" or "determining" or the like, refer to the action and processes of a computer system, or similar electronic computing device, that manipulates and transforms data.

Skin is the body's largest organ. It accounts for 12-16% of body weight and made up of a complex mosaic of four layers, the stratum corneum, epidermis, dermis and subdermis layers. Many internal diseases are known to distinctively affect the skin. The skin has a principal role in thermoregulation and water-balance. The skin is also a vital tactile sensory organ, and its mechanical characteristics greatly affect the nature of the neural patterns which occur where it makes contact with an object. For example, neural mechanoceptors (corpuscles) detect superficial and deep pressure such as brushing, vibration, flutter, and indentation. Temperature (thermoreceptors) and pain (noiceptor), are detected by different sets of electric receptors. These skin sensors, along with muscle/joint position awareness or proprioception (proprioceptors), male up the mosaic of somatic senses. Receptors convey this information to the spinal cord and brain, by converting, mechanical, thermal, or chemical energy into electrical signals. Thus, the skin contains many neurally connected and interacting structures, e.g., sweat glands.

Sweat glands form the largest exocrine glands of the body. At least 2 types of sweat glands are distinguished concerning development, morphology and function: eccrine sweat glands forming the majority and apocrine sweat glands which are present just in limited areas.

Eccrine sweat glands are distributed all over the body surface with high density at certain regions like the face, palms and soles of the feet. FIG. 1 illustrates an example of distribution of sweat pores radius on a patch of skin of a human thumb.

Generally, three types of perspiration are known, these are thermoregulatory, gustatory and emotional sweating. In particular, perspiration from eccrine sweat glands provides important temperature regulation. It is also known that perspiration can be induced by stress, emotion and disease, as well as physical exercise (see, for example, Ohhashi, et al., *Physiol. Meas.*, 1998, V. 19, PP. 449-461).

These roles are intimately associated with the activity of the sweat glands whose neurally controlled activity influences thermal balance through evaporative heat loss. A central nervous system thermostat in the hypothalamus regulates the function of the eccrine sweat glands. Perspiration is controlled by sympathetic nervous system via the cholinergic fibres that innervate the sweat glands.

Figure 2:
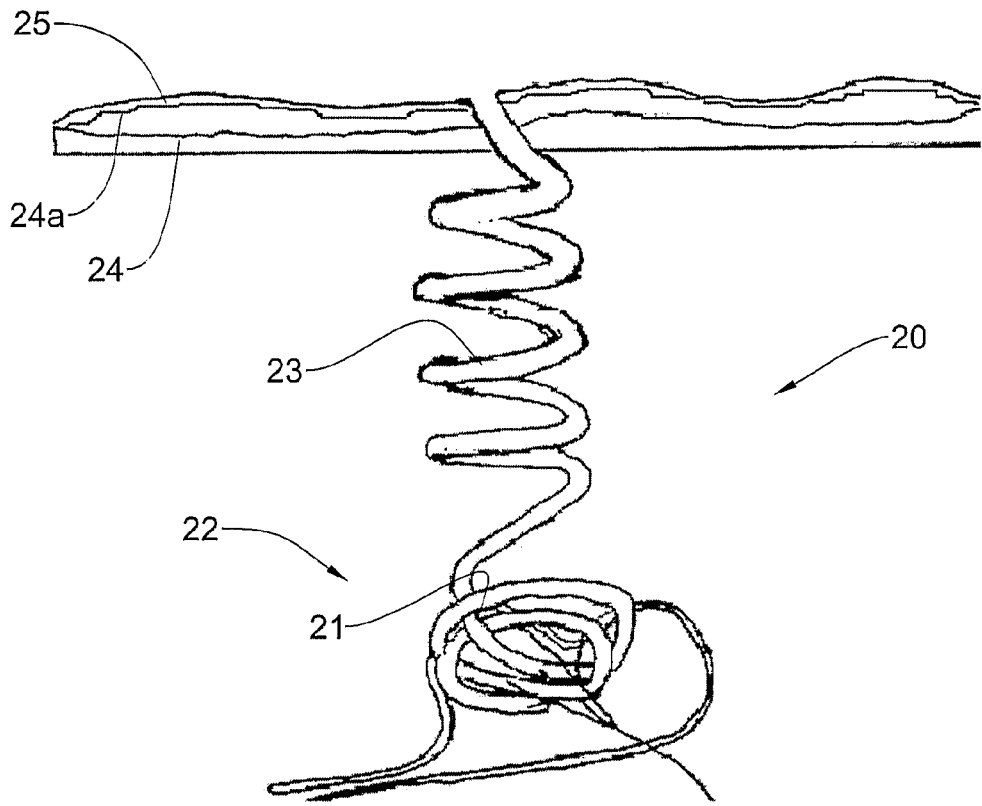
FIG. 2 is a schematic illustration of a skin element including an eccrine sweat gland.

Referring to FIG. 2, an eccrine sweat gland 20 includes a secretory coil 21 arranged deep in a dermis 22 and a duct 23 which transverses skin from the inner pail of the dermis 22 to cornified layers of an epidermis 24 and a stratum corneum 24a, and then conveys the secreted sweat to a skin surface 25 via the duct 23. The sweat ducts 23 are in the shape of coiled tubes.

The present invention exploits the fact that bioelectric activity of eccrine sweat glands imitates the behavior of RCL resonant circuits. It should be noted, however, that the basal flow rates associated with sweat are slow compared to the characteristic frequencies of resonance, derived from the dimensions of the spiral structure of the duct, which are in the range of about 10 microns to 100 microns. Hence, it is unlikely that sweat flow is the driving mechanism of these RCL circuits, however it can provide a contribution in the modulation of the electromagnetic waves generated by the sweat glands.

Furthermore, it is known that biological cells can, inter alia, transmit an electrical signal via gap junctions. Such junctions, residing on the cell surface, can be found in almost all animal tissues, and also in sweat glands (see, for example, Granger et al., *Am. J. Physiol. Cell Physiol.*, 2003, V. 285, PP. C1047-C1058). Gap junctions can provide a faster mechanism for propagating action potentials than the chemical synapses. In particular, chemical synapses have a typical delay of 0.5 milliseconds while electrical synapses (the main constituent of a gap junction) of less than $10^{-13}$ seconds.

Likewise, the aqueous interior of cells in the surface of the sweat duct can allow the formation of stable hydrogen bonded networks. Hence, coherent proton transfer along such networks can occur. The characteristic time for such transfer is in the region of $10^{-13}$ seconds. Therefore, the surface current along the cells of the spiral sweat duct can be considered as instantaneous and the resonant frequency of the gland would be determined by the geometric structure of the ducts.

As a result, the electromagnetic radiation generated by the sweat glands can be extremely high frequency (EHF) carrier waves in the range of 30 GHz to 1 THz (corresponding to the millimeter through submillimeter wavelength range) modulated by low frequency information signals reflecting a condition of the living organism, e.g., physiological condition and emotional state.

It should be appreciated that the described mechanisms of the charge carriers responsible for generation of the electromagnetic waves related to the sweat glands do not limit generality of the description. Furthermore, there is no intention to be bound by any type of charge carriers and/or theory describing the phenomenon of the waves generation presented in the description.

Figure 3:
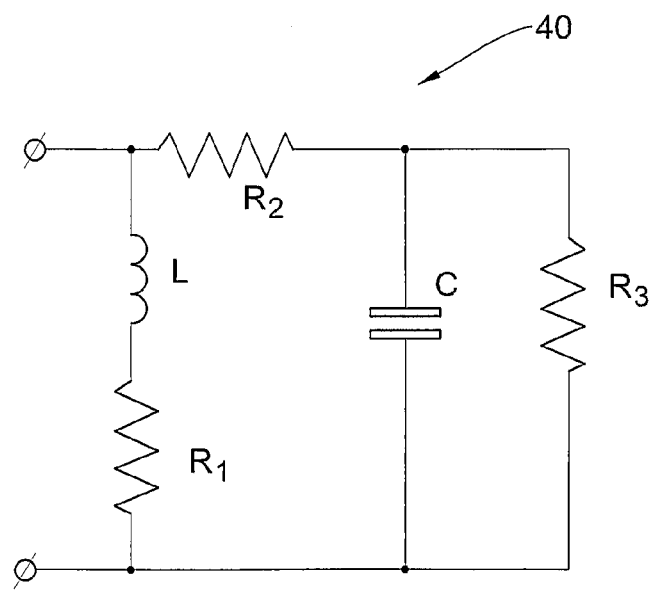
FIG. 3 illustrates an equivalent electric circuit of a single eccrine sweat gland, in accordance with an embodiment of the invention.

Referring to FIG. 2 and FIG. 3 together, in accordance with an embodiment of the invention, electric properties of the skin element with the eccrine gland 20 can be represented by an electric circuit 40, wherein the duct 23 can be approximated by an equivalent circuit element that includes an inductive element containing a coil with inductance L connected in series to a resistor $R_1$, so that the equivalent impedance is given by $Z_1 = R_1 + i\omega L$. The inductance L of the sweat gland can be obtained by $$L = \mu_0 \frac{N^2 A}{h},$$

where N is the number of turns, A is the cross section area of the duct, and h is the height of the duct 23.

The cornified layers of the epidermis 24 can be approximated by a circuit element including a capacitor C connected in parallel to a resistor $R_3$, so that the overall impedance is given by $$Z_3 = \frac{R_3}{1 + i\omega R_3 C}.$$

Accordingly, the resistance of the skin surface can be approximated by a shunt resistor $R_2$. The shunt resistor $R_2$ is connected in series with impedance circuit $Z_3$, so their combined impedance is given by $Z_2 = R_2 + R_3$.

The resulting entire impedance of this skin element is then $$Z^*(\omega) = \frac{Z_1 Z_2}{Z_1 + Z_2}$$

Figure 4:
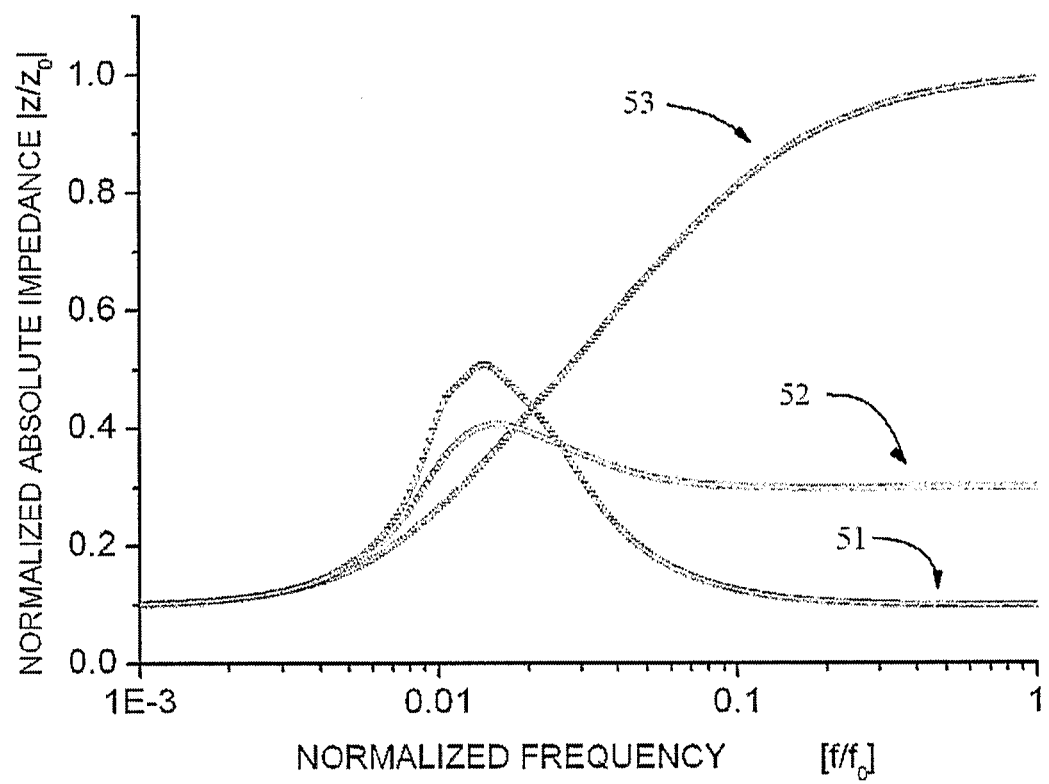
FIG. 4 illustrates an example of simulations of the frequency dependence of the module of the entire impedance of a skin element including an eccrene sweat gland.

Referring to FIG. 4, an example of simulations of the frequency dependence of the module of the entire impedance $|Z^*|$ is shown for different values of the resistance $R_2$ of the skin surface, in accordance with the above electrical model of the eccrine sweat gland. The simulation was carried out under the assumption of the lumped elements of the electric circuit (40 in FIG. 4). It should be appreciated by a person versed in the art that the assumption of lumped elements may be considered rather reasonable as a first approximation, because the ratio of the duct dimensions (which are about 100 µm) to the resonant wavelengths (which are about 1 mm) of the structures is relatively small (i.e., about 0.1). In the simulation, the values of the electrical parameters C, $R_1$, and $R_3$ of the model were kept unchangeable and set to the following magnitudes: $C = 2.310^{-16}$F; $R_3 = 100$ kΩ; $R_1 = 1$ kΩ. For estimation of inductance L, the following geometrical parameters of the duct of the eccrine sweat gland were kept constant: N=4 and h=100 µm. A distribution of the cross sectional area of the ducts has been considered on the basis of the distribution of sweat pores shown in FIG. 1.

The resistance $R_2$ of the skin surface is substantially affected by the amount of sweat produced by the glands. Therefore, $R_2$ can be varied in a relatively broad range. The following values were selected for the simulation, 1 kΩ (curve 51), 3 kΩ (curve 52), and 10 kΩ (curve 53). As can be seen in FIG. 4, the effect of the resistance $R_2$ is dramatic. As $R_2$ is reduced (see curve 51) that corresponds to stronger sweating through the pores, the resonant spectrum is resolved. Additionally, such a sweat flow could be responsible for amplitude modulation and low frequency modulation of the produced high frequency carrier wave, and can reflect an organism condition, e.g., physiological condition and emotional state of the living organism.

In order to demonstrate the validity of the proposed electric model of the sweat gland and the above simulations a measurement of the electromagnetic radiation reflection coefficient of a human palm was carried out. The hand was fixed to an absorbing back plate and screened from external radiation sources. The measurements were conducted at a distance of 30 cm from the subject using a horn antenna having a 3 cm² aperture connected to a microwave generator and a Network analyzer. The frequency band swept was 75 GHz-110 GHz. To account for parasitic reflections and diffraction effects, the measured spectrum was compared with the water phantom spectrum measured in the same configuration.

Figure 5A:
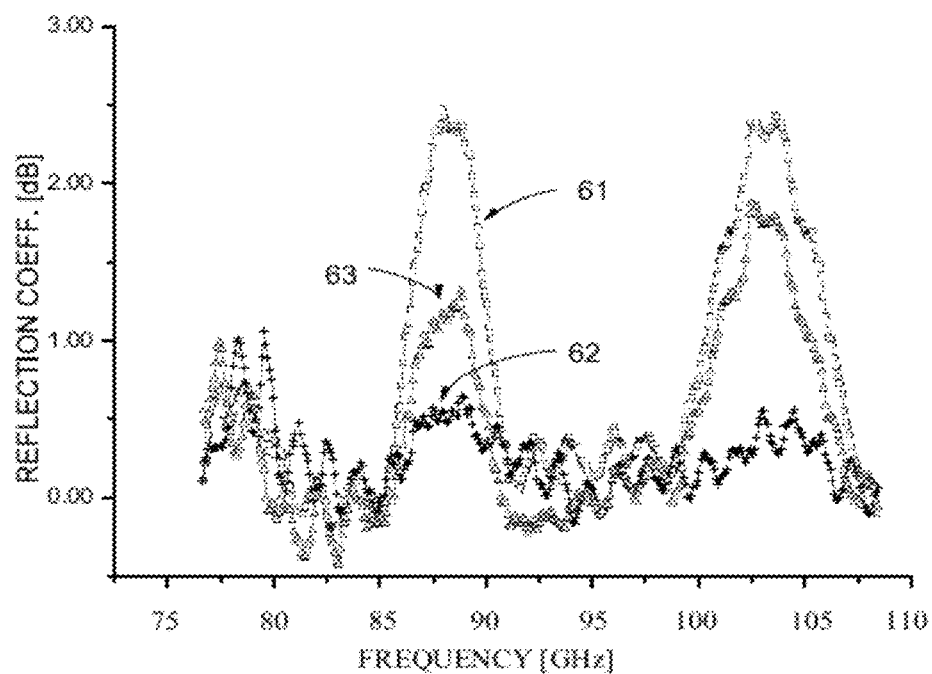
FIG. 5A illustrates various examples of the frequency dependence of the reflection coefficient for different conditions of a hand.

Referring to FIG. 5A, examples of the frequency dependence of the reflection coefficient are shown for three different conditions of a hand. A curve 62 corresponds to the measurements of the hand in a cool state with little or no surface sweat; a curve 63 corresponds to the measurements of the hand in a warmed state with surface dampness evident, and a curve 61 corresponds to the measurements of the hand in a warmed state with surface sweat evident. The difference in skin temperature of the hand in cool and warm conditions was 1 K.

As can be seen, in the frequency range measured two distinct peaks are noticed in the reflection spectra of the subject. One peak is in the range of 86 GHz-90 GHz and another peak is in the range of 102 GHz-107 GHz. It can be seen that the signal strength is increased as sweating increases, confirming the validity of the electric sweat gland model described above.

Figure 5B:
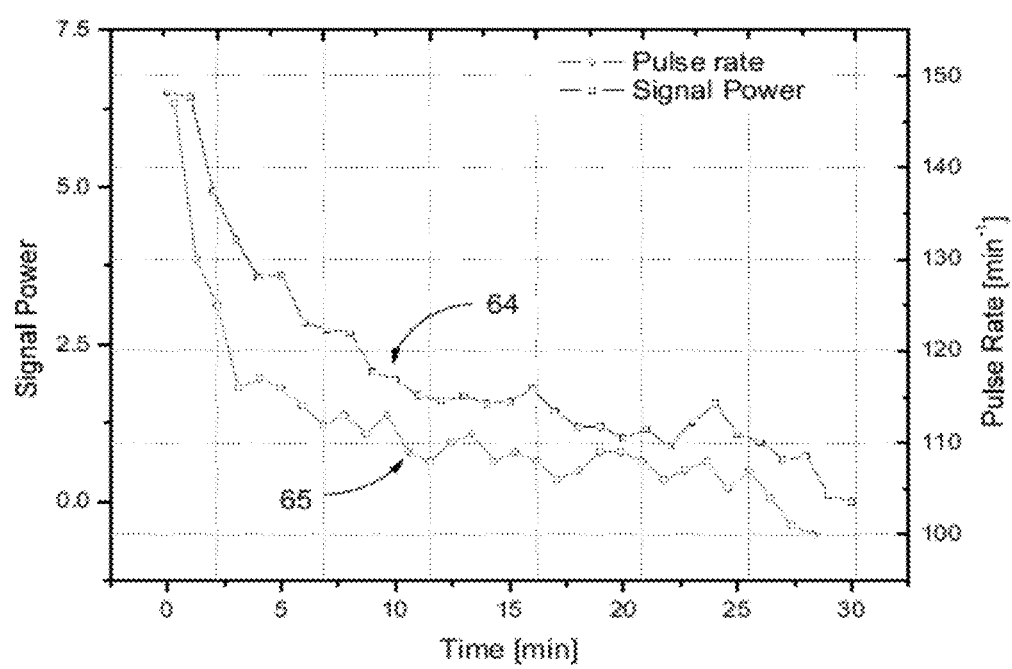
FIG. 5B illustrates examples of the time behaviors of the signal power obtained from the reflection coefficient of a person's hand and a concurrent pulse of the same person at rest following intense exercise.

Referring to FIG. 5B, an example of the time behavior of the function $W(t) = \langle I \rangle_{max} - \langle I(t) \rangle$ (curve 64) is shown. The signal power $\langle I(t) \rangle$ is obtained from reflection coefficient measurements in the frequency band 75 GHz-110 GHz of a hand of a person at rest following 20 minutes of intense exercise. For comparison, the time behavior of the person's pulse (curve 65) is illustrated. The signal power was calculated from the reflection intensity (which is proportional to $|R|^2$) over the frequency band $[f_1; f_2]$, to with:

$$\langle I(t) \rangle = \int_{f_1}^{f_2} |R(f, t)|^2 \, df$$

To avoid reflection from surface water the hand was dried. As can be seen, the behavior of the signal power correlates with the behavior of the relaxation curve of the subject's pulse up to regular calm levels.

The electromagnetic radiation pattern generated by the sweat glands depends on their structure and morphology. It is known that there are between 2 and 4 million sweat glands on a human body, and their spatial distribution in the skin, the size of the ducts and the number of the turns are unique to the individual. Thus, the radiation pattern associated with the sweat glands is also unique to the individual. The radiation pattern is indicative of the organism condition (e.g., physiological condition, emotional state of the living organism) and can be utilized for identification, as will be described hereinbelow. Examples of physiological condition include, but are not limited to, the conditions caused by exercise, hot weather, humidity, illness, puberty, menopause, menstruation, metabolism, etc. Examples of emotional state include, but are not limited to, stress, anxiety, fear, anger, nervousness, embarrassment, panic, general neurological disorders, etc. It is also known that hot drinks, spicy foods, certain medications and certain illicit drugs can cause bioelectric activity of the sweat glands (gustatory sweating) indicated by the corresponding radiation pattern.

Moreover, various diseases are known to influence the sweat gland complex, which would lead to a disease specific change in the radiation pattern associated with the sweat glands. Examples of the diseases include, but are not limited to, fever, flu, cold, pneumonia, malaria, severe pain, hypoglycemic attack, AIDS, hyperhidrosis, anhidrosis, cancer, Frey's syndrome, etc. The detected radiation patterns can be indicative of the corresponding diseases of the living-organism, and can thus be utilized for diagnostics.

According to one aspect of the invention, the concept of detection of electromagnetic waves produced as a result of bioelectric activity of eccrine sweat glands is utilized for the detection in a passive mode.

Figure 6:
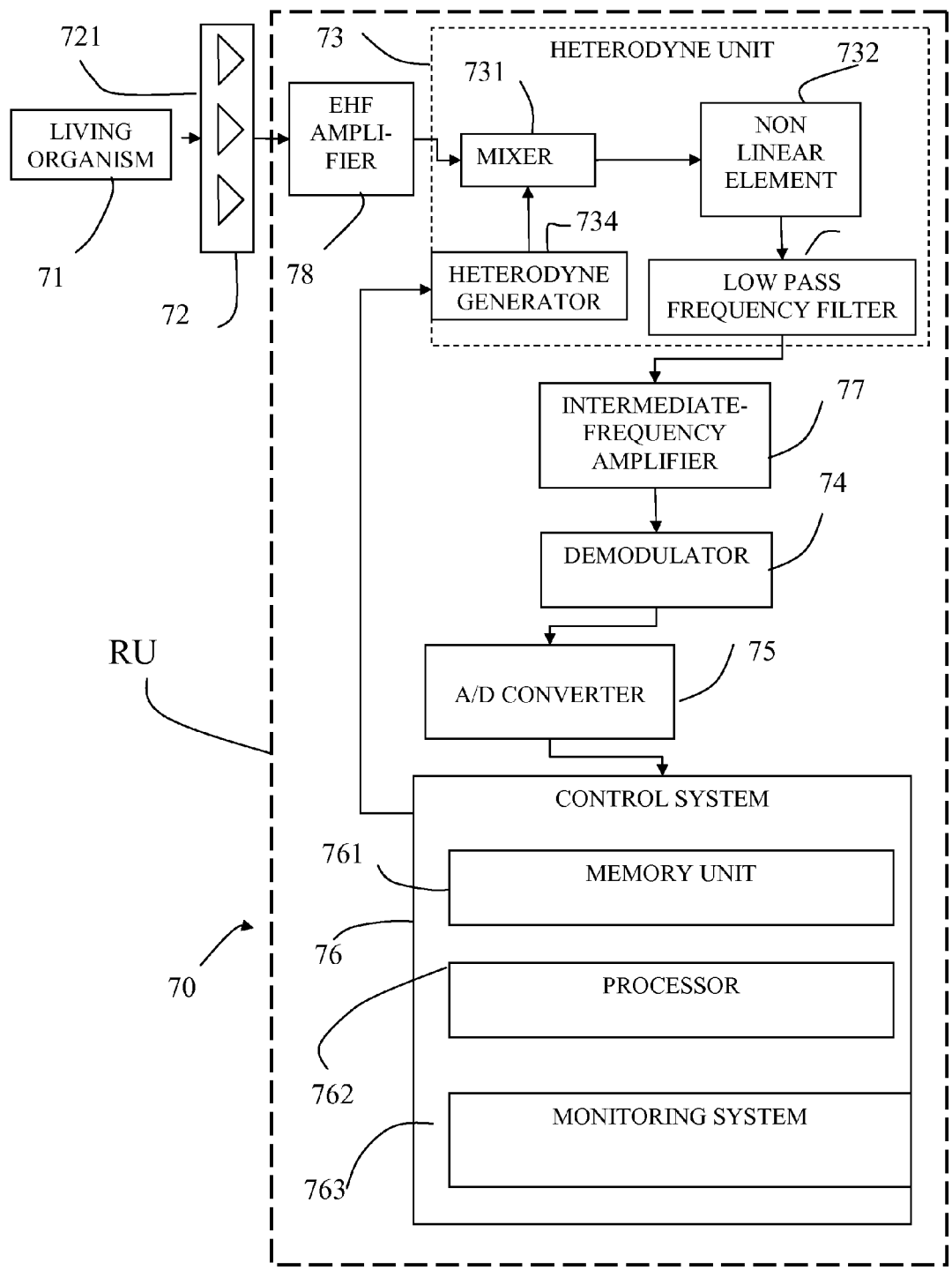
FIG. 6 illustrates an exemplary system operating in a passive mode for non-invasive detection of electromagnetic waves produced as a result of bioelectric activity of eccrine sweat glands of a living organism.

FIG. 6 illustrates an exemplary system 70 for non-invasive detection of electromagnetic waves produced as a result of bioelectric activity of eccrine sweat glands (not shown) of a living organism 71. The system is implied for passive detection, namely is configured to operate in a receiving mode only, and includes an antenna array unit 72 and a receiving unit RU coupled to the antenna array unit 72.

The antenna array unit 72 includes one or more antennas (three such antennas 721 are shown in the present example), and is accommodated with respect to the living organism such that the antennas are dispersed along the surface of the skin. Each antenna 721 is configured for sensing electromagnetic waves in the extremely high frequency (EHF) range of 30 GHz to 1 THz emanated from a corresponding skin portion of the living organism 71. The antenna array unit 72 is operable to produce an extremely high frequency (EHF) electrical signal based on the sensed electromagnetic waves. Examples of the antennas 721 in the antenna array unit 72 suitable for the purpose of the present invention include, but are not limited to, horn antennas, slot antennas, strip antennas, parabolic antennas, etc. The extremely high frequency electromagnetic signal produced by the antenna array unit 72 is informative of a condition of the living organism.

The receiving unit RU is configured for receiving and analyzing the EHF electromagnetic signal produced by the antenna array unit to generate output date indicative of the current condition of the living organism. The receiving unit RU includes a heterodyne unit 73 coupled to the antenna array unit 72, a demodulator 74 arranged downstream of the heterodyne unit 73, an analog-to-digital (A/D) converter 75 coupled to the demodulator 74, and a control system 76 coupled to the A/D converter 75.

It should be noted, although not specifically shown, that the system 70 can be housed inside of a shielding cage (e.g., a Faraday cage), in order to prevent the measurements from being affected by the environment.

The heterodyne unit 73 includes a heterodyne generator 734, a mixer 731 coupled to the heterodyne generator 734, a non-liner element 732 coupled to the mixer 731, and a low pass filter 733 downstream of the non-liner element 732. The heterodyne unit 73 is operable to transfer the EHF electromagnetic signal from its extremely high carrier frequency band to a lower frequency band to produce an intermediate frequency electrical signal. The heterodyning is accomplished by mixing the original EHF signal with a sine wave generated by the heterodyne generator 734 to produce an intermediate frequency electrical signal maintaining the information of the original EHF electromagnetic signal. The heterodyning process is well known per se, and therefore will not be expounded hereinbelow in detail.

According to one embodiment of the invention, the demodulator 74 is appropriately configured for demodulation of the intermediate frequency electrical signal. It should be understood that the signal associated with the bioelectric activity of eccrine sweat glands may be amplitude, frequency and/or phase modulated. For example, the amplitude modulation can be associated with the different rate of the sweat flow. In turn, the variations of the geometric and electric parameters of the ducts may cause the frequency and phase modulations of the high frequency electrical signal. Accordingly, the demodulator 74 can be configured to provide all or at least one of these three types of modulation.

As a result of the demodulation process, a relatively low frequency information signal is generated which represents at least one modulation function (amplitude A, frequency $\omega$ and/or phase $\phi$) of the high frequency carrier waves generated by the eccrine sweat glands. In a general case, the low frequency information signal represents a combination of amplitude, frequency and phase modulation functions.

The A/D converter 75 is operable to convert the information signal provided by the demodulator 74 from an analog form to a digital form, thereby to produce a digitalized information signal. Accordingly, this digitalized information signal is fed to the control unit 76.

The control system 76 is typically a computer system having, inter alia, such known utilities as a memory unit 761, a processor 762 (data acquisition and processing utility), and a monitoring system 763 configured for presenting the detected results. The processor 762 is preprogrammed by a suitable software model capable of analyzing the received data (i.e., output information signal of the A/D converter 77) and determining one or more desired biometric signatures associated with the radiation originated from the sweat glands, as will be described herebelow. The monitoring system 763 can include a display, printer and/or other monitoring devices (not shown).

Preferably, but not mandatory, the receiving unit RU further includes an intermediate frequency amplifier 77 arranged downstream of the heterodyne unit 73 and configured for amplifying said intermediate frequency electrical signal, thereby to produce an amplified intermediate frequency electrical signal which is more suitable for a further signal processing.

When required, the receiving unit RU can further include an extremely high frequency (EHF) amplifier 78 arranged downstream of the antenna array before the heterodyne unit 73.

It should also be understood that when required, the analyzing of the digitalized information signal can include broad-band filtering the information signal by utilizing a low pass and/or high pass filters (not shown).

According to one embodiment of the invention, the analyzing of the digitalized information signal and determining biometric signatures can be carried out in frequency domain. In this case, an example of the biometric signature is a frequency spectrum of the digitalized information signal.

An example of the biometric signature includes, but is not limited to, a frequency spectrum in terms of intensity of the digitalized information signal $U(\omega)$ obtained by $$S(\omega)=U(\omega)U^*(\omega),$$

where the superscript asterisk denotes the complex conjugate.

The inventors have found that the frequency spectra associated with the sweat glands substantially depend on the sweat related conditions of the living organism. Moreover, the frequency spectra have similar features for similar sweat related conditions. Thus, each sweat related condition can be matched with the corresponding specific pattern of the frequency spectra. In other words, the specific physiological condition and/or emotional state of the organism can be characterized by the behavior of the frequency spectra.

Figure 7A:
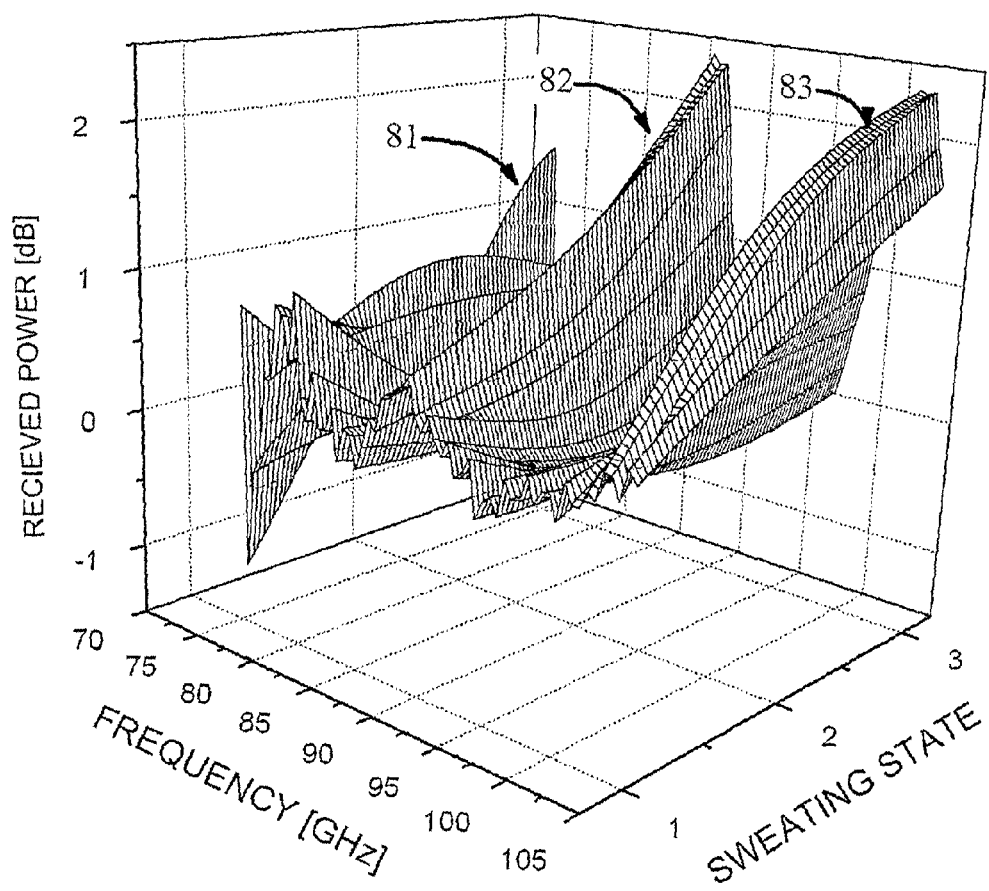
FIGS. 7A and 7B illustrate examples of 3D frequency spectra pattern and 3D time autocorrelation function pattern of the digitized information signal, respectively as a function of sweating state.

Referring to FIG. 7A, an example of a pattern of a 3D frequency spectrum $S(\alpha, \omega)$ of a hand is shown versus different sweating state $\alpha$ of the hand that corresponds to three different organism conditions. In particular, a state 1 corresponds to a dry hand, a state 2 corresponds to moderately damp hand, and a state 3 corresponds to a heavily sweating hand The frequency spectrum $S(\alpha, \omega)$ is characterized by three main peaks 81, 82 and 83. Parameters characterizing behavior of the frequency spectrum, such as magnitudes (intensities) of the peaks 81, 82 and 83, locations of the peaks on the frequency spectra (i.e., the frequency values at which the peaks occur), and Q-factors of the peaks substantially depend on the sweating state of the hand. Therefore, these parameters can be used for identification of a mental state of the subject. Thereafter, these parameters characterizing behavior of the frequency spectrum will be referred to as biometric characteristic parameters.

As can be understood by a person versed in the art, corresponding frequency spectra $S(x, y, \omega, A, \phi)$ can be created for a portion of the skin, where x and y are the two dimensional coordinates on the skin portion with respect to a reference point. When required, the frequency spectra $S(x, y, \omega, A, \phi)$ can be mapped on an image (picture) of the living organism and visualized on the display of the monitoring system (763 in FIG. 6). For example, the amplitude modulation function can be visualized by variation of image brightness (or intensity); the frequency modulation function can be visualized by variation of color; while the phase modulation function can be visualized by variation of picture contrast. Accordingly, changes of at least one sweat related condition of the organism can result in the changes of the brightness, color and/or contrast of the image of the skin portion.

According to another embodiment of the invention, the analyzing of the digitalized information signal and determining biometric signatures can be carried out in time domain. In this case, the control system operates to process the frequency spectrum $S(\omega)$ through the Fourier transform for obtaining the biometric signatures in the form of time autocorrelation function of the digitalized information signal, to with:

$$F^{-1}(S(\omega)) \equiv \frac{1}{2\pi} \int_{-\infty}^{\infty} d\omega S(\omega) \exp[-i\omega t] = \Psi(t)$$

Examples of the biometric characteristic parameters derived from the time autocorrelation function include, but are not limited to, the amplitude of the correlation function $\psi(0)$ and effective correlation time of the peak $$\tau = \frac{1}{\Psi(0)} \int_0^\infty \Psi(t) dt.$$

Figure 7B:
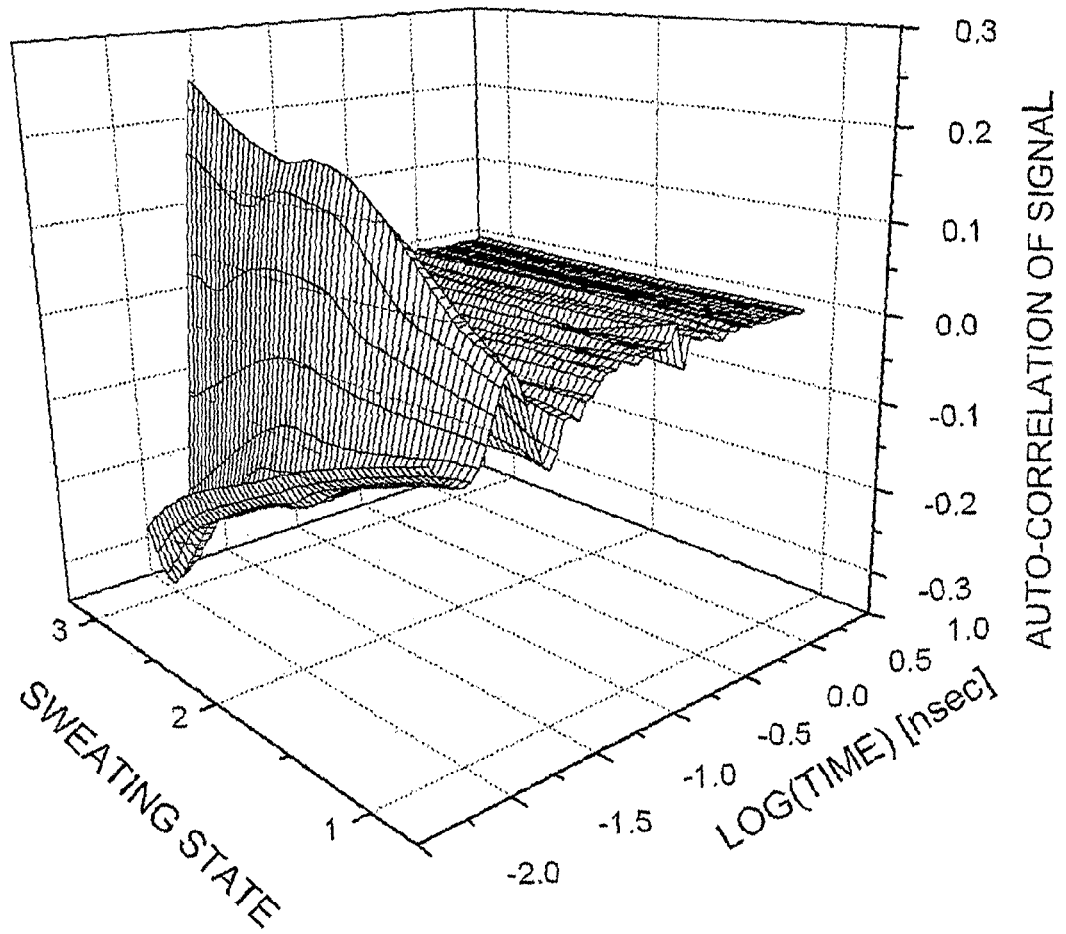

Referring to FIG. 7B, an example of a pattern of a 3D time autocorrelation function $\psi(\alpha, t)$ of the digitalized information signal of a hand is shown versus different sweating state $\alpha$ of the hand that corresponds to the same three different organism conditions as described above with reference to FIG. 7A. As can be seen, the most apparent is a peak centered around 0.1 nanoseconds, with the peak amplitude increasing with increase in sweating. Peaks of longer duration are less evident.

In practice, a database (reference data) of various biometric signatures (e.g., frequency spectra patterns, time autocorrelation functions) and characteristic parameters (location, magnitude and Q-factor of the peaks on frequency spectra patterns; and amplitude of the correlation function and effective correlation time of the peaks on autocorrelation function patterns) derived from the signatures can be created for each subject of interest (living organism), and then stored in the memory unit (761 in FIG. 6) of the control system (76 in FIG. 6), thereby each living organism can be cataloged. This database can include records establishing the correlations between the unique biometric signatures and their parameters and various conditions (physiological and emotional) associated with the organism. Due to the potentially sensitive nature of such personal information, when required, the data in the database may be processed through an encryption algorithm, and also stored in the memory unit of the control system.

According to one aspect of the invention, the data presented in this database can be used for a personal identification of the organism.

Figure 8:
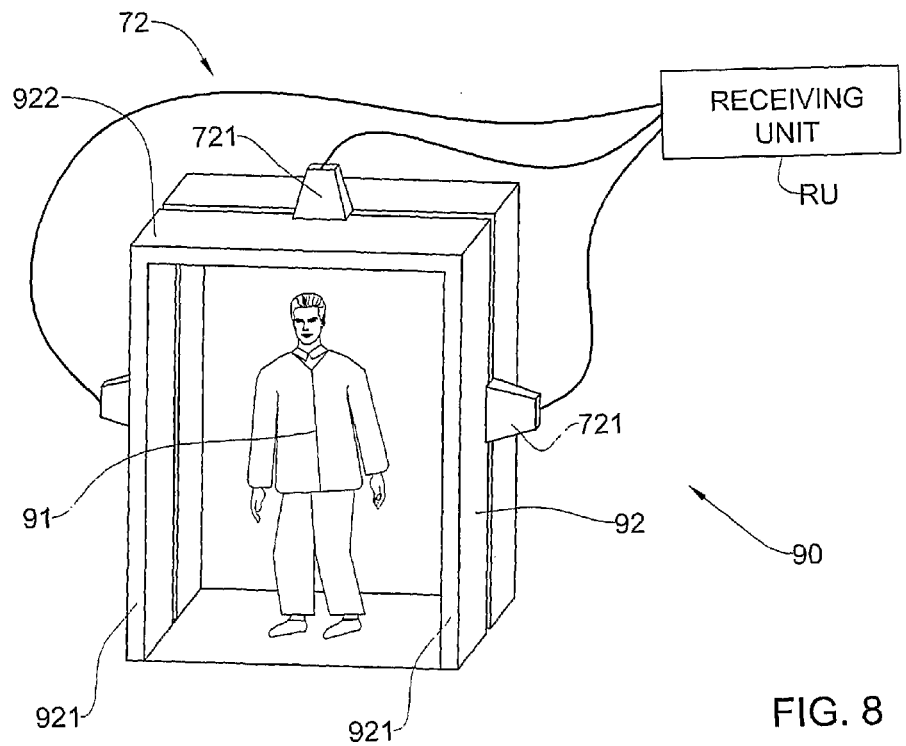
FIG. 8 illustrates an exemplary configuration of the detection system of the present invention designed for identification of a living organism.

Referring to FIG. 8, an exemplary configuration of a detection system 90 of the present invention designed for identification of a subject of interest (living organism) 91 is illustrated. According to this embodiment, the detection system 90 is configured generally similar to the above-described system (70 in FIG. 6) and is associated with a door frame tunnel gate 92 through which the subject 91 can pass. Sides 921 and a top 922 of the door frame tunnel gate 92 maintain an antenna array unit 72 having a series of antennas (e.g., horn antennas) 721 configured to sense the extremely high microwave frequency range (millimeter and sub-millimeter wavelength), as described above with reference to FIG. 6. The antennas 721 are appropriately distributed with respect to the gate 92.

When the detection system of the present invention is used for identification, certain reference data sensitive to organism individuality should be provided. The reference data can, inter alia, include the unique biometric signatures, their characterizing parameters and a spectral image associated with the organism. According to one embodiment, the reference data can be obtained by detecting electromagnetic radiation for a certain group of specific living organisms subjected to various organism conditions (e.g., calm and nervous emotional state) and stored in the memory unit (761 in FIG. 6) in a database catalog form. According to another embodiment, the reference data can be obtained by developing and employing generic physiological models describing human psychological and emotional state.

In operation, when the subject of interest 91 (individual) passes the door frame tunnel gate 92, the extremely high frequency electrical signal produced by the antenna array unit 72 is processed by the detection system 90, as described above, to obtain the unique biometric signatures and/or the corresponding biometric characterizing parameters of the individual. Thereafter, one or more biometric signatures and/or the characterizing parameters can be compared with those stored in the memory unit (761 in FIG. 6) for estimating to which organism from the certain group these data correspond, thereby identifying the organism and his current physiological condition and/or emotional state. Likewise, images of the organism in which the frequency spectra are visualized, as described above, can be used for the identification purpose by comparing the obtained images to the cataloged biometric images of the subject, previously stored in the memory unit. The correlation between the images can be done by using any known suitable image recognition technique.

According to another aspect of the invention, the cataloged biometric signatures and characteristic parameters can be matched with different diseases and stored in the memory unit. These data can be utilized as reference data for diagnostics of the organism.

In operation, predetermined reference data sensitive to organism individuality and indicative of different diseases from a predetermined list of diseases should be provided.

Then, one or more biometric signatures or characterizing parameters derived from the biometric signatures obtained from the detection in accordance with the invention can be compared with the predetermined reference data. Thereafter, estimation can be performed from this comparison to which of the diseases from the predetermined list of diseases these biometric signatures and/or characterizing parameters correspond.

Figure 9:
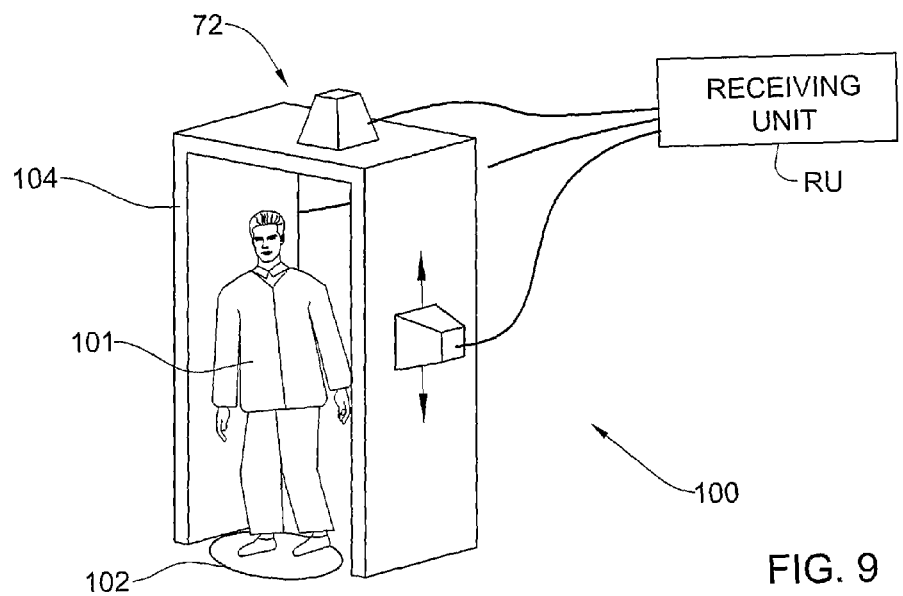
FIG. 9 illustrates an exemplary configuration of the detection system of the present invention designed for diagnostics of a living organism.

Referring to FIG. 9, an exemplary configuration of a detection system 100 of the present invention designed for diagnostics of a subject of interest (living organism) 101 is illustrated. This configuration differs from that shown in FIG. 9 in that the detection system further includes a revolving base plate 102.

In operation, a subject (living organism) 101 stands inside a door frame tunnel gate 104, and elements of the antenna array unit 72 are vertically moved from head to foot perpendicular to the subject's body. The subject 101 is revolved with the base plate 102 in coordination with the antenna movement, and the electromagnetic pattern of the subject can be detected in the same passive mode as described above for identification. The demodulated information signal is relayed to the control unit for further analysis for receiving one or more biometric signatures and their characterizing parameters which, in turn, can be compared to cataloged signatures and parameters of particular illnesses, or alternatively measured against empirical models.

According to another aspect of the invention, the concept of detection of electromagnetic waves produced as a result of bioelectric activity of sweat glands can also be utilized for the detection in an active mode.

Figure 10:
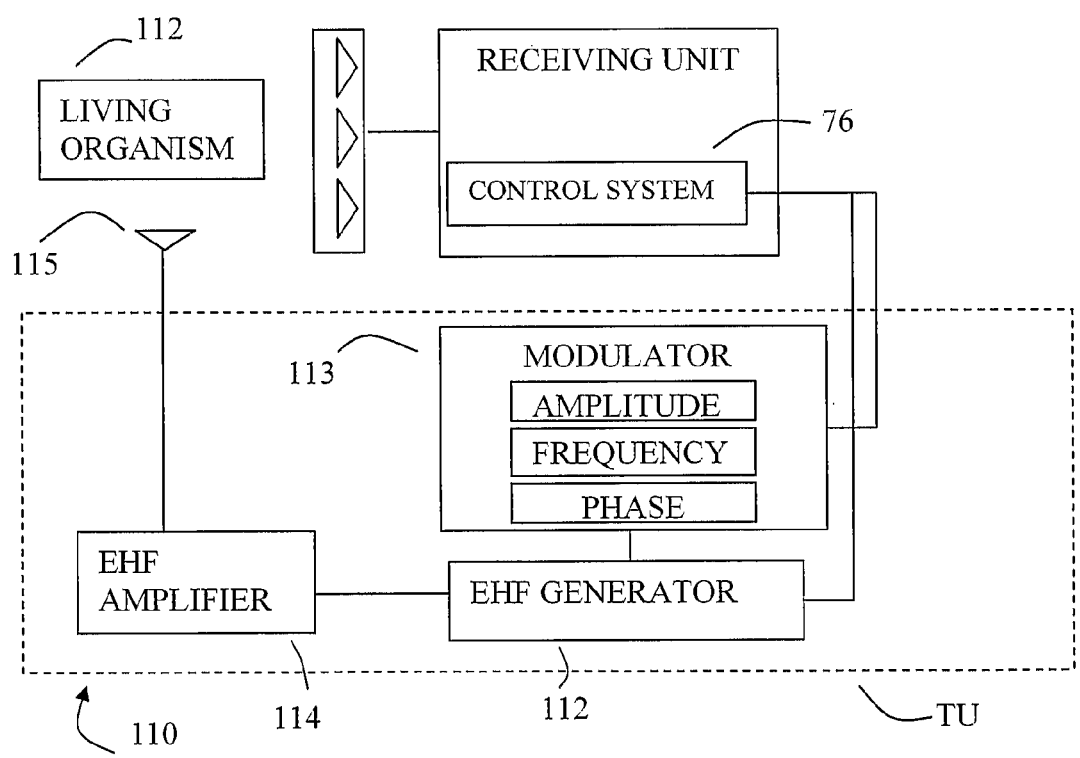
FIG. 10 illustrates an exemplary system operating in an active mode for detection of electromagnetic waves produced as a result of bioelectric activity of eccrine sweat glands in a skin portion of a living organism.

Referring to FIG. 10, an exemplary system 110 for detection of electromagnetic waves produced as a result of bioelectric activity of eccrine sweat glands (not shown) in a skin portion of a living organism 111 is illustrated, in accordance with this aspect of the invention.

The system 110 includes all the units of the passive detection system (70 in FIG. 6), and further comprises a transmitting unit TU coupled to the control system 76. The control system 76 is configured further for generating various control signals required for operating the transmitting unit TU, as will be described hereinbelow. The transmitting unit TU includes an extremely high frequency (EHF) signal generator 112 coupled to the control system 76, a modulator 113 coupled to the EHF signal generator 112 and the control system 76, and a transmitting antenna unit 115 (including a single antenna or antenna array) coupled to the EHF amplifier 115. When required, an extremely high frequency (EHF) amplifier 114 downstream of the EHF generator 112 can also be arranged.

The EHF generator 112 is responsive to a switch control signal provided by the control system 76 and operable to generate a HF carrier signal sampled over time which includes a train of pulses of predetermined high frequencies $f_1, f_2, \ldots, f_n$, as selected by an operator (not shown). The number n of the frequencies is dictated by the frequency range $[f_1, f_n]$ selected for the scanning and by an interval (increment) between two neighboring frequencies. For example, the lowest frequency $f_1$ can be about 30 GHz, the highest frequency $f_n$ can be about 1000 GHz, and the intermediate frequencies can be selected in accordance with an increment of 1 GHz. The EHF generator 112 can, for example, be based on a backward wave oscillator or on other conventional suitable EHF generator of sampled analogous signals.

The modulator 113 is responsive to a modulation control signal provided by the control system 76 and configured for applying a low frequency information signal which is represented by at least one predetermined modulation function to the EHF generator 112. Thus, the low frequency information signal is superimposed upon the EHF carrier signal to modulate it. Three types of modulation functions can be considered providing phase, amplitude and frequency modulations, respectively. The type of modulation is defined by the modulation control signal generated by the control system 76. According to one example, all the predetermined high frequencies $f_1, f_2, \ldots, f_n$ are modulated by the same predetermined modulation function. According to another example, each frequency or at least some of the frequencies are modulated by different modulation functions.

When required to synthesize complicated information signals for some of the applications, the modulator 113 can also include a harmonic mixer (not shown) configured for mixing harmonics of the modulation signal before relaying the modulation function to the EHF generator 112.

The HF amplifier 114 can be configured for amplifying the EHF frequency modulated signals provided by the EHF signal generator 112, and relaying the amplified frequency signals to the transmitting antenna unit 115. The transmitting antenna unit 115 is configured for generating and radiating electromagnetic waves based on the EHF frequency modulated signals towards the living organism.

In operation, the electromagnetic waves based on the EHF frequency modulated signals are applied to a portion of the skin having eccrine sweat glands distributed therein. This radiation will be either absorbed by or reflected from the skin portion, and thus can be detected by the system 110, as described above with reference to FIG. 6. Accordingly, the detected signal can be utilized for identification and diagnostics of the living organism.

It is likewise possible to employ a predetermined modulated electromagnetic wave in the millimeter to sub-millimeter wavelength range (30 GHz-1 THz) for therapeutic treatment. In particular, the predetermined modulated electromagnetic wave being an extremely high frequency carrier signal modulated by a predetermined information signal can be applied to the skin of the living organism. The predetermined information signal can include information for modifying the organism condition, such as physiological condition and emotional state.

Moreover, the applying of electromagnetic waves can be utilized for correcting the bioelectric activity of the organism via the sweat glands, and thereby providing therapeutic treatment to the organism. In such a case, the amplitude, frequency and/or phase modulation functions detected from a healthy organism can be used for modulating the EHF signal generated by the EHF generator 112. When such an EHF signal modulated by a modulation function bearing the information of a healthy organism is applied to an ill organism, this information can be conveyed to the spinal cord and brain to regulate the functioning of the organism.

Those skilled in the art to which the present invention pertains, can appreciate that while the present invention has been described in terms of preferred embodiments, the concept upon which this disclosure is based may readily be utilized as a basis for the designing of other structures, systems and processes for carrying out the several purposes of the present invention.

Also, it is to be understood that the phraseology and terminology employed herein are for the purpose of description and should not be regarded as limiting.

Finally, it should be noted that the word "comprising" as used throughout the appended claims is to, be interpreted to mean "including but not limited to".

It is important, therefore, that the scope of the invention is not construed as being limited by the illustrative embodiments set forth herein. Other variations are possible within the scope of the present invention as defined in the appended claims and their equivalents.

The invention claimed is:

1. A method for non-invasive determination of at least one condition of a living organism selected from physiological conditions and emotional states of the living organism, the method comprising:

sensing electromagnetic waves in an extremely high frequency (EHF) band emanated or reflected from the living organism, said sensing comprising sweeping at least a portion of said EHF band and obtaining an electromagnetic radiation pattern for said at least a portion of the EHF band, the electromagnetic waves including radiation originated from spiral sweat ducts of sweat glands distributed in a skin portion of the living organism, the radiation being indicative of an information signal related to bioelectric activity of said sweat ducts; and obtaining from the information signal related to bioelectric activity of said spiral sweat ducts at least one unique biometric signature of the living organism indicative of said at least one organism condition by:

producing an extremely high frequency (EHF) signal based on the sensed electromagnetic waves in said at least a portion of the EHF band, the EHF signal including an EHF carrier electromagnetic signal modulated by the information signal related to bioelectric activity of spiral sweat ducts;

heterodyning the EHF signal from its extremely high carrier frequency band to a lower frequency band to produce an intermediate frequency electrical signal;

demodulating said intermediate frequency electrical signal to provide said information signal representing at least one modulating function selected from a amplitude modulating function, a frequency modulating function, and a phase modulating function;

converting said information signal from analog form to digital form to produce a digitalized information signal; and analyzing said digitalized information signal for determining said at least one biometric signature.

2. The method of claim 1 wherein said extremely high frequency band is in the range of 30 GHz through 1 THz.

3. The method of claim 1 wherein the analyzing of said digitalized information signal includes broad-band filtering said digitalized information signal.

4. The method of claim 1 wherein the analyzing of said digitalized information signal is carried out in frequency domain, thereby obtaining the biometric signatures in the form of a frequency spectrum of said digitalized information signal.

5. The method of claim 4 further comprising mapping said frequency spectrum on an image of said skin portion for visualizing changes of said at least one organism condition.

6. The method of claim 1 said wherein the analyzing of said digitalized information signal is carried out in time domain, wherein the analyzing includes processing the digitalized information signal through the Fourier transform, thereby obtaining the biometric signatures in the form of an autocorrelation function of said digitalized information signal.

7. The method of claim 1 wherein the analyzing of said digitalized information signal includes determining at least one biometric characteristic parameter derived from said at least one biometric signature.

8. The method of claim 7 wherein at least one biometric characteristic parameter is an element selected from the list including location, magnitude and Q-factor of peaks on frequency spectra patterns; and amplitude of the correlation function and effective correlation time of the peaks on autocorrelation function patterns.

9. The method of claim 1 wherein the analyzing of said digitalized information signal includes creating a database containing at least one record establishing correlation between said at least one biometric signature and the corresponding organism condition.

10. The method of claim 1 comprising amplifying said intermediate frequency electrical signal to produce an amplified intermediate frequency electrical signal before said converting.

11. The method of claim 1 further comprising carrying out the following before or after said sensing:

preparing a predetermined modulated high frequency signal being an EHF carrier signal modulated by a predetermined low frequency information signal;

generating a predetermined modulated electromagnetic wave based on the modulated EHF signal; and applying said predetermined modulated electromagnetic wave to said skin portion.

12. The method of claim 11 wherein the preparing of said predetermined modulated EHF signal includes: generating the EHF carrier signal sampled over time which includes at least one pulse of a predetermined extremely high frequency; and superimposing said predetermined low frequency information signal upon the EHF carrier signal.

13. The method of claim 12 wherein said predetermined low frequency information signal includes information for modifying said at least one organism condition.

14. The method of claim 12 wherein said predetermined low frequency information signal includes information for providing a therapeutic treatment to said living organism.

15. The method of claim 1 utilized for identification of the living organism, the method further comprising: providing predetermined reference data including at least one biometric signature or at least one characterizing parameter derived therefrom for each organism of a group of living organisms; comparing said at least one biometric signature or at least one characterizing parameter of the living organism under identification with said predetermined reference data; and estimating from this comparison to which of the organisms from said group of living organisms said at least one biometric signature or at least one characterizing parameter corresponds.

16. The method of claim 1 utilized for diagnostics of at least one conditional state of said living organism, the method further comprising:

providing predetermined reference data including at least one biometric signature or at least one characterizing parameter derived therefrom corresponding to each conditional state from a predetermined list of conditional states;

comparing said at least one determined biometric signature or characterizing parameter of the living organism under diagnostics with said predetermined reference data; and analyzing the comparison results and estimating to which of the conditional states from the predetermined list of conditional states said at least one determined biometric signature or characterizing parameter corresponds.

17. The method of claim 16, wherein the conditional state is a healthy state.

18. The method of claim 16, wherein the conditional state is disease.

19. The method of claim 1 utilized to determine which condition the living organism has, the method further comprising: (a) providing predetermined reference data of at least one biometric signature or at least one characterizing parameter derived therefrom for a plurality of living organisms diagnosed for a first condition, (b) repeating step (a) to provide a series of reference data, each corresponding to a different condition; (c) comparing said at least one biometric signature or at least one characterizing parameter derived therefrom of the living organism under examination with each one of said predetermined reference data in said series; (d) determining which reference data has statistically significant similarity with the biometric signature or the characterizing parameter of the living organism under examination, the condition of the living organism being the condition for which said reference data has statistically significant similarity.

20. The method of claim 19 wherein said different conditions correspond to different diseases.

21. A system for non-invasive determination of at least one condition of a living organism selected from physiological conditions and emotional states of the living organism, the system comprising:
- an antenna array unit configured for sensing electromagnetic waves in an extremely high frequency (EHF) band emanated or reflected from the living organism by sweeping at least a portion of said EHF band, obtaining an electromagnetic radiation pattern for said at least a portion of the EHF band, and producing a EHF electromagnetic signal based on the sensed electromagnetic waves, said EHF electromagnetic signal including a EHF carrier signal modulated by a low frequency information signal originated from spiral sweat ducts of sweat glands distributed in a skin portion of the living organism; and
- a receiving unit coupled to the antenna array and configured and operable for obtaining from said EHF electromagnetic signal based on sensed electromagnetic waves at least one unique biometric signature of said living organism indicative of said at least one organism condition,
wherein said receiving unit further includes:
  - a heterodyne unit coupled to the antenna array, said heterodyne unit being operable to transfer the EHF electromagnetic signal from its extremely high carrier frequency band to a lower frequency band to produce an intermediate frequency electrical signal;
  - a demodulator downstream of the heterodyne unit, said demodulator configured for demodulating said intermediate frequency electrical signal to provide said information signal representing at least one modulating function selected from an amplitude modulating function, frequency modulating function, and phase modulating function an analog-to-digital (A/D) converter downstream of the demodulator and configured for converting said information signal from analog form to digital form to produce a digitalized information signal; and
  - a control system coupled to the A/D converter and configured for analyzing said digitalized information signal for determining said at least one biometric signature.

22. The system of claim 21 wherein said extremely high frequency band is in the range of 30 GHz through 1 THz.

23. The system of claim 21 wherein said receiving unit further comprises an intermediate frequency amplifier arranged downstream of the heterodyne unit and configured for amplifying said intermediate frequency electrical signal to produce an amplified intermediate frequency electrical signal.

24. The system of claim 21 wherein said receiving unit further comprises an EHF frequency amplifier arranged downstream of the antenna array and upstream of the heterodyne unit, and said EHF frequency amplifier configured for amplifying said EHF electromagnetic signal before feeding thereof to said heterodyne unit.

25. The system of claim 21 wherein said heterodyne unit includes a heterodyne generator, a mixer coupled to the heterodyne generator, a non-liner element coupled to the mixer and a low pass filter downstream of the non-liner element.

26. The system of claim 21 wherein said control system comprises a memory unit for storing predetermined reference data including at least one biometric signature or at least one biometric characterizing parameter derived therefrom for each organism of a group of living organisms.

27. The system of claim 26 wherein said control system is further configured for comparing said at least one biometric signature or at least one characterizing parameter of a living organism under identification with said predetermined reference data; and estimating from this comparison to which of the organisms from said group of living organisms said at least one biometric signature or at least one characterizing parameter corresponds, thereby to provide identification of said living organism.

28. The system of claim 21 wherein said control system comprises a memory unit for storing predetermined reference data including at least one biometric signature or at least one biometric characterizing parameter derived therefrom corresponding to each conditional state from a predetermined list of conditional states.

29. The system of claim 28 wherein said control system is further configured for comparing said at least one biometric signature or at least one characterizing parameter of a living organism under diagnostics with said predetermined reference data; and estimating from this comparison to which of the conditional states from the predetermined list of conditional states said at least one biometric signature or at least one characterizing parameter corresponds, thereby to provide diagnostics of said living organism.

30. The system of claim 21 further comprising:
- a transmitting unit coupled to the control system, said transmitting unit includes: an EHF signal generator coupled to the control system and responsive to a switch control signal provided thereby, said EHF signal generator being operable to generate an EHF carrier signal sampled over time which includes at least one pulse of a predetermined extremely high frequency;
- a modulator coupled to the EHF signal generator and the control system, said modulator being responsive to a modulation control signal provided by the control system and configured for applying a predetermined low frequency information signal which is represented by at least one predetermined modulation function to the EHF generator to modulate said EHF carrier signal; and
- a transmitting antenna unit coupled to the modulator and configured for generating and radiating electromagnetic waves based on the EHF frequency modulated signals towards the living organism.

31. The system of claim 30 wherein said predetermined low frequency information signal includes information for modifying said at least one organism condition.

32. The system of claim 30 wherein said predetermined low frequency information signal includes information for providing a therapeutic treatment to said living organism.

* * * * *